United States Patent
Owner-Petersen et al.

(10) Patent No.: US 7,639,369 B2
(45) Date of Patent: Dec. 29, 2009

(54) MULTI-OBJECT WAVEFRONT SENSOR WITH SPATIAL FILTERING

(76) Inventors: Mette Owner-Petersen, Omebakken 63, Gl. Holte 2840, Holte (DK); Jorgen Thaung, Asa Backv.53, 430 31 Asa (SE); Zoran Popovic, Killingegangen 27, 426 71 V.Frolunda (SE)

( * ) Notice: Subject to any disclaimer, the term of this patent is extended or adjusted under 35 U.S.C. 154(b) by 245 days.

(21) Appl. No.: 11/786,404

(22) Filed: Apr. 11, 2007

(65) Prior Publication Data
US 2007/0247638 A1  Oct. 25, 2007

Related U.S. Application Data

(60) Provisional application No. 60/791,727, filed on Apr. 13, 2006.

(51) Int. Cl.
*G01B 11/02* (2006.01)
*A61B 3/10* (2006.01)

(52) U.S. Cl. .................................. 356/512; 351/211

(58) Field of Classification Search ......... 356/511–512; 351/210–212
See application file for complete search history.

(56) References Cited

U.S. PATENT DOCUMENTS

| | | | |
|---|---|---|---|
| 5,629,765 A * | 5/1997 | Schmutz | 356/121 |
| 6,338,559 B1 * | 1/2002 | Williams et al. | 351/212 |
| 6,382,795 B1 * | 5/2002 | Lai | 351/212 |
| 6,634,750 B2 * | 10/2003 | Neal et al. | 351/211 |
| 6,890,076 B2 * | 5/2005 | Roorda | 351/205 |
| 2004/0130705 A1 * | 7/2004 | Topa | 356/121 |
| 2007/0171366 A1 * | 7/2007 | Su et al. | 351/205 |

* cited by examiner

*Primary Examiner*—Michael A Lyons
(74) *Attorney, Agent, or Firm*—Lynn E. Barber

(57) ABSTRACT

The present invention relates to an adaptive optics sensor intended for simultaneous detection of several wavefronts on a common camera target. The sensor is intended for use in connection with multi-conjugate adaptive optics (MCAO), where several wavefront measurements are needed at the same time. The sensor includes a spatial filter taking out signals resulting from parasitic reflections of the reference sources and from unwanted parts of the object.

8 Claims, 4 Drawing Sheets

MULTI-OBJECT WAVEFRONT SENSOR WITH SPATIAL FILTERING

CROSS-REFERENCE TO RELATED APPLICATIONS

This application claims priority from U.S. provisional application Ser. No. 60/791,727 filed Apr. 13, 2006, which is incorporated herein by reference.

BACKGROUND OF THE INVENTION

1. Field of the Invention

The present invention relates to a high-resolution wide field adaptive optics imaging system based on a compact multi-reference wavefront sensor.

The shortcomings of single reference systems in the severely restricted field of corrected view is solved with multi-conjugate adaptive optics (MCAO) systems; however this is at high cost and gives bulky instruments, especially problematic in ophthalmology. Another problem, especially in the study of the human eye, is unwanted light from parasitic source reflections and light from unwanted object regions.

2. Description of the Related Art

The main purpose of an adaptive optics (AO) system is to correct for dynamical optical aberrations that blur the image of a normally extended object under investigation. Typical examples of such images are ground based telescope images blurred by the atmosphere and retinal images blurred by the eye's optical aberrations. Related to a perfect image point there will be a spherical wavefront converging towards the point. A wavefront is the locus (a line or surface in an electromagnetic wave) of points having the same phase. When the image point is blurred by aberrations, the corresponding wavefront will deviate from the perfect one, and the difference between the two wavefronts is called the wavefront aberration. Conventional AO systems comprise a wavefront sensing arm measuring the wavefront and a science arm used for imaging and other measurement purposes. A so-called Shack-Hartmann wavefront sensor in the wavefront sensing arm usually makes use of a point source, located somewhere within the image to be corrected, to estimate the wavefront. The aberrated wavefront associated with this point source is measured by subdividing it into small regions subjected only to local tilt. From each of these small regions, an image of the reference source is formed. These images will be translated according to the local wavefront tilt, which can then be measured. The collection of point images is called a Hartmann pattern. A wavefront modulating device is inserted in the part of the optical path common to both the wavefront sensing arm and the imaging arm. This can be either a deformable mirror or a reflective or transmitting phase modulator. Hence the sensor works in a closed loop where the original aberrations are cancelled by the wavefront modulating device. Conventional AO suffers from the drawback that if the image aberrations vary over the image, a single wavefront modulator will correct only a small region around the location of the reference source. Having more than one modulating element can extend the corrected image region, but this also requires more than one reference source. Such a scheme is called multi-conjugate adaptive optics (MCAO).

Wavefront sensing and AO have caused a renaissance of vision research. Collaborations with astronomy research groups have been instrumental in developing AO systems for ophthalmology and vision science. Confocal scanning laser ophthalmoscopes have been available for some time for imaging the retina. The resolution achieved by these instruments is limited by aberrations in the cornea and lens of the eye. By including AO correction in a scanning laser ophthalmoscope, it is possible to correct these aberrations and so obtain diffraction-limited images of the retina. These reveal the fine structure of the eye, including individual photoreceptors, blood vessels, and nerve fibers. Early studies have revealed new information about the organization and function of the retina, changes indicating disease and the optical and neural limits of human vision.

The resolution of the eye is potentially affected by retinal resolution and neural factors as well as by optical aberrations. Studies with AO corrected instruments suggest that even sharper resolution can be obtained by correcting higher-order aberrations in the eye. Spectacles have been used for centuries to correct defocus. It is only in the last 150 years that spectacles have been used to also correct astigmatism. Adaptive optics systems offer the possibility of accurately measuring high-order aberrations in individuals and customizing the correction to each person. Methods for implementing this are currently being explored; customized contact lenses, intraocular lenses, or customized laser refractive surgery.

The ability to image individual photoreceptors in the living eye may also improve our ability to diagnose eye disease. Age-related macular degeneration (AMD) is a disorder of the macula, a small area at the very center of the retina responsible for our sharpest vision, in which damage to the photoreceptor layer causes severe vision loss in the elderly. The early stages of AMD comprise pigmentary changes and drusen development, which contrasts with the more severe forms that develop geographic. atrophy or neovascular membranes. It is this early form of AMD that is important, as it heralds the loss of a normal retinal status and indicates a greater risk to central vision loss. Glaucoma, a disease in which blindness ensues from the gradual loss of optic nerve fibers, can only be detected with conventional imaging techniques after a significant amount of damage has already occurred. More accurate measurement of the nerve fiber layer thickness around the optic nerve head will allow earlier detection of this disease. Diabetes is another disease that affects the retina by the formation of microaneurysms in the retinal vasculature. Treatment requires accurate delivery of a photocoagulating laser beam, which could benefit from a higher resolution view of the critical retinal region.

Today, no commercial AO corrected ophthalmic instruments are available. The first research instruments used low-order deformable mirrors for aberration correction, typically 37-actuator faceplate mirrors. Higher order correction systems are now in use. These typically use 97-actuator deformable faceplate mirrors that are so large that they require elaborate beam expansion optics. These systems are expensive and bulky, which makes them unsuitable for clinical applications. The push in this area is now towards Micro Electro-Mechanical Systems (MEMS) deformable mirrors that are much smaller and cheaper than piezo-electrically driven faceplate mirrors. The availability of suitable MEMS devices will revolutionize the market for clinical adaptive optics corrected ophthalmoscopes.

Adaptive correction of the eye was first attempted in 1989 by Dreher (Dreher, A. W. et al. Appl Opt, 1989. 28(4): p. 804-) who used a 13-actuator segmented mirror to correct a subject's astigmatism by applying his conventional prescription for spectacles for adjustment of the mirror form. Liang (Liang, J. et al. J Opt Soc Am A, 1997. 14(11): p. 2884-92) constructed an AO system that could correct higher order aberrations using a large 37-actuator single sheeted deformable mirror (made by Xinetics Inc). Vargas-Martin (Vargas-Martin, F. et al. J Opt Soc Am A, 1998. 15(9): p. 2552-62)

evaluated the performance of a liquid crystal spatial light modulator for the correction of aberrations in the human eye. These examples all used static AO wavefront correction, e.g. optical aberrations of an eye were first measured using a wavefront sensing device, and the obtained information was subsequently applied to a deformable mirror or spatial light modulator.

Ocular aberrations, however, are dynamic. Aberrations change over time, with, for example, accommodation (the eye's lens change of focus), and with gaze angle. There is thus a need for real-time AO correction, as demonstrated by Fernandez (Fernandez, E. J. et al. Optics Letters, 2001. 26(10): p. 746-748) and Hofer (Hofer, H. et al. Optics Express, 2001. 8(11): p. 631-643). There are also dynamic processes occurring in the retina that, if they are to be studied in detail, require the implementation of real-time AO correction. The AOSLO (Roorda, A. et al. Optics Express, 2002. 10(9): p. 405-412), a confocal scanning laser ophthalmoscope with AO correction, is a good example of an instrument built for the purpose of studying dynamic processes. It is capable of high frame rate imaging in living human eyes of photoreceptors and of blood cells, thus enabling direct measurements of blood flow (Martin, J. A. et al. Ophthalmology 2005. 112(12): p. 2219-2224), as well as optical sectioning of the retina (Venkateswaran, K. et al. J. Biomed. Opt. 2004. 9(1): p. 132-138; Zhang, Y. et al. J. Biomed. Opt. 2006. 11, 014002). A combination of AO and ultrahigh resolution optical coherence tomography (UHR OCT) (Hermann, B. et al. Optics Letters 2004. 29(18): p. 2142-2144) has been shown to substantially increase sensitivity in comparison to standard UHR OCT and to enable unprecedented identification of intraretinal layers in the living eye with axial and transverse resolutions on the order of a few microns.

Correction, or manipulation, of the eye's aberrations with AO is central to new instruments for imaging the retina, and is critical to experiments that explore both optical and neural mechanisms in vision. MCAO has not yet been introduced but has been regarded as the next challenge in ophthalmologic AO to achieve higher resolutions over larger fields of view. Recent MCAO advancements have been made within the field of astronomy (Kelly, T. et al. Opt Express, 2000. 7: p. 368-374; Owner-Petersen, M., and Goncharov, A. J. Opt. Soc. Am. A, 2002. 19(3): p. 537-548; Knutsson, P. and Owner-Petersen, M. Opt. Express, 2003. 11: p. 2231-2237; Goncharov, A. J. et al. Opt. Express 13: p. 5580-5590).

U.S. Pat. No. 6,452,146 describes a method for the control of two phase correction devices, but it does not show the present invention using a collimator array and one camera.

U.S. Pat. No. 6,199,986 describes a method for measurement of the eye's wave aberration; however this patent does not disclose the present invention using multiple guide star sources or the present invention using a collimator array and one camera, nor does it show the present invention using a single spatial filter to simultaneously reduce unwanted light from parasitic source reflections and light from unwanted object regions from all guide stars to improve image quality in the wavefront sensor camera.

U.S. Pat. No. 6,634,750 and patent application US 2003/0038921 present an invention for a tomographic wavefront analysis system, but they do not show the present invention using a collimator array and a single spatial filter to simultaneously reduce unwanted light from parasitic source reflections and light from unwanted object regions from all guide stars to improve image quality in the wavefront sensor camera.

U.S. Pat. No. 6,736,507 presents an invention for a high resolution, multispectral, wide field of view retinal imager, but it does not show the present invention using two deformable mirrors to correct for aberrations over a wider field of view, nor does it show the present invention using a collimator array and a single spatial filter to simultaneously reduce unwanted light from parasitic source reflections and light from unwanted object regions from all guide stars to improve image quality in the wavefront sensor camera.

U.S. Pat. No. 6,964,480 presents an invention for a multiple stage phase compensator wavefront analysis system, but it does not show the present invention using a collimator array and a single spatial filter to simultaneously reduce unwanted light from parasitic source reflections and light from unwanted object regions from all guide stars to improve image quality in the wavefront sensor camera.

Goncharov et al (11 Jul. 2005/Opt. Express 13: p. 5580-5590) presents a MCAO system for telescopes using five reference sources and two deformable mirrors for multi-pupil imaging on a single detector, but they do not present the solution of our invention to use a collimator array and a single spatial filter to reduce unwanted light from parasitic source reflections and light from unwanted object regions to get sufficient image quality for human retina studies.

Normally in MCAO systems, each reference source will require its own wavefront sensor making the optical setup both bulky and expensive. The purpose of the sensor of the invention described here is both to place all Hartmann patterns on a single camera, and to clean them from spurious contributions.

Therefore, it is an object of this invention to provide a method and a product using multi-reference adaptive optics systems with spatial filtering to accurately and dynamically measure high-order aberrations in living human eyes. Aberrations change over time, with for example accommodation (the eye's lens change of focus), and with gaze angle and an individual's heartbeat. There is thus a need for real-time MCAO correction, enabling improved direct detailed studies, measurements and optical sectioning of the human retina.

Another object of this invention for correcting aberrations over a larger area in a living eye is to improve our ability to diagnose eye disease. Age-related macular degeneration is a disorder of the very center of the retina responsible for our sharpest vision, in which damage to the photoreceptor layer causes severe vision loss in the elderly. Improved retinal imaging is a key issue for early detection of this disease. Diabetes is another disease that affects the retina by the formation of microaneurysms in the retinal vasculature. Treatment requires accurate delivery of a photocoagulating laser beam, which could benefit from a higher resolution view of the critical retinal region. Glaucoma, a disease in which blindness ensues from the gradual loss of optic nerve fibers, can only be detected with conventional imaging techniques after a significant amount of damage has already occurred. More accurate measurement of the nerve fiber layer thickness around the optic nerve head will allow earlier detection of this disease.

Another object of this invention is to provide a method using multi-reference adaptive optics systems to accurately measuring high-order aberrations in individuals and customizing the correction to each person. Methods for implementing this are currently being explored: customized contact lenses, intraocular lenses, or customized laser refractive surgery.

Another object of this invention is to use the herein described methods for aberration correction and filtering of unwanted light from parasitic source reflections and light from unwanted object regions to provide improved image quality and analysis from retinal scans for biometric purposes.

SUMMARY OF THE INVENTION

The shortcomings of single reference systems in the severely restricted field of corrected view is solved with multi-conjugate adaptive optics (MCAO) systems, however this is at high cost and gives bulky instruments, especially problematic in ophthalmology. Another problem, especially in the study of the human eye is unwanted light from parasitic source reflections and light from unwanted object regions. The present invention solves both these problems by firstly using an array of collimator lenses making it possible to spatially filter the light from all guide stars using one variable pinhole, and secondly this arrangement makes it possible to use a single camera to image the Hartmann patterns of multiple reference sources.

Possible implementation in for example commercial, equipment for wide field retinal imaging is foreseen.

Figure 1A:
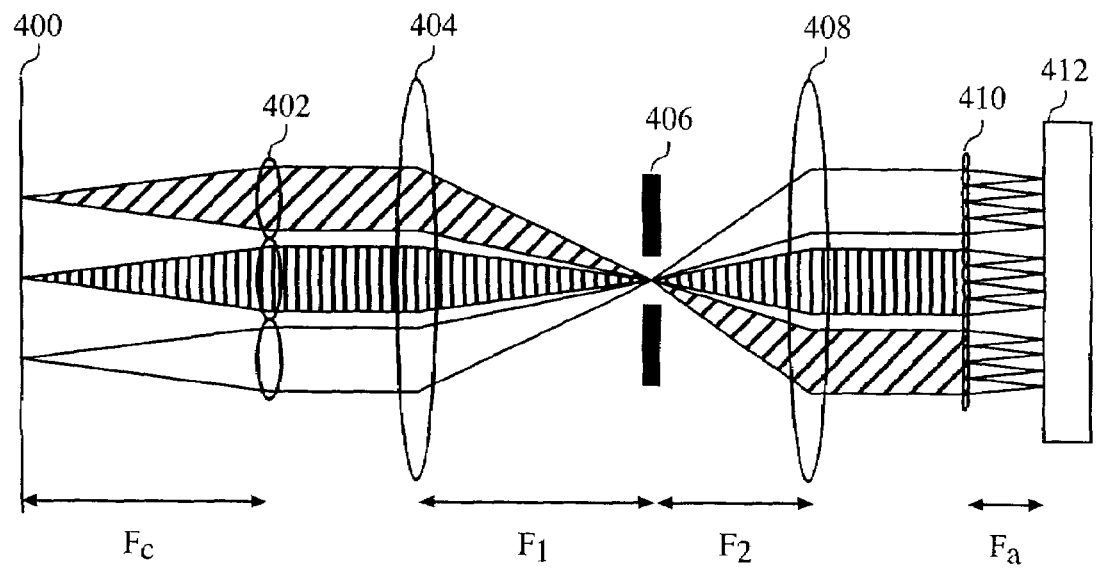
FIG. 1a shows the layout of the multi-object wavefront sensor. The front focal plane 400 for the sensor is a telecentric image plane for the reference sources meaning that the pupil is at infinity. The source images are aberrated and the corresponding wavefronts are the subjects of the measurement. An array 402 of collimator lenses is arranged in a pattern to match the positions of the reference sources. The individual collimator elements should not be overfilled by the ray-cones emerging from the sources. Thus, their size is matched to the focal ratio of the sources.

Lens 404 focuses all source images on top of each other on the optical axis in the plane of the variable pinhole 406, centered on the optical axis. At the beginning of a measurement session it should be sufficiently large to pass the aberrated source images, but may be narrowed down when closed loop operation narrows down the source images. The purpose of the variable pinhole is to block unwanted light from parasitic source reflections and light from unwanted object regions.

Lens 408 images the sources at infinity and matches the ray-pattern to the camera target 412. Microlens array 410 provides the subdivision of the wavefronts associated with each source and re-images the reference sources on the camera target 412, providing output for wavefront control and analysis.

$F_c$ is the focal length of the elements of the collimator array 402. $F_1$ is the focal length of lens 404. $F_2$ is the focal length of lens 408. $F_a$ is the focal length of the individual lens elements in the microlens array 410. The distances between elements 402 and 404 as well as elements 408 and 410 may be adjusted to provide pupil images on the microlens array 410.

Figure 1B:
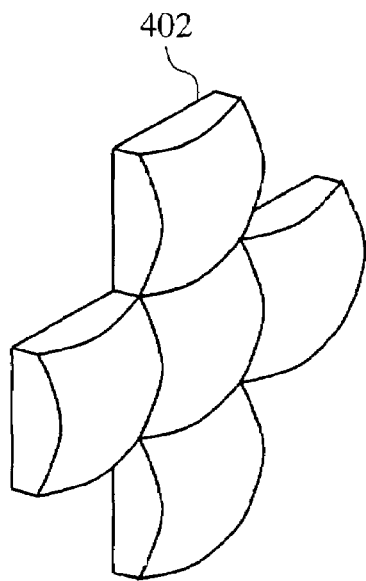

FIG. 1b shows the layout of the collimating lens array 402, which in the setup in Example 1 is rotated 45 degrees with respect to the drawing.

Figure 2:
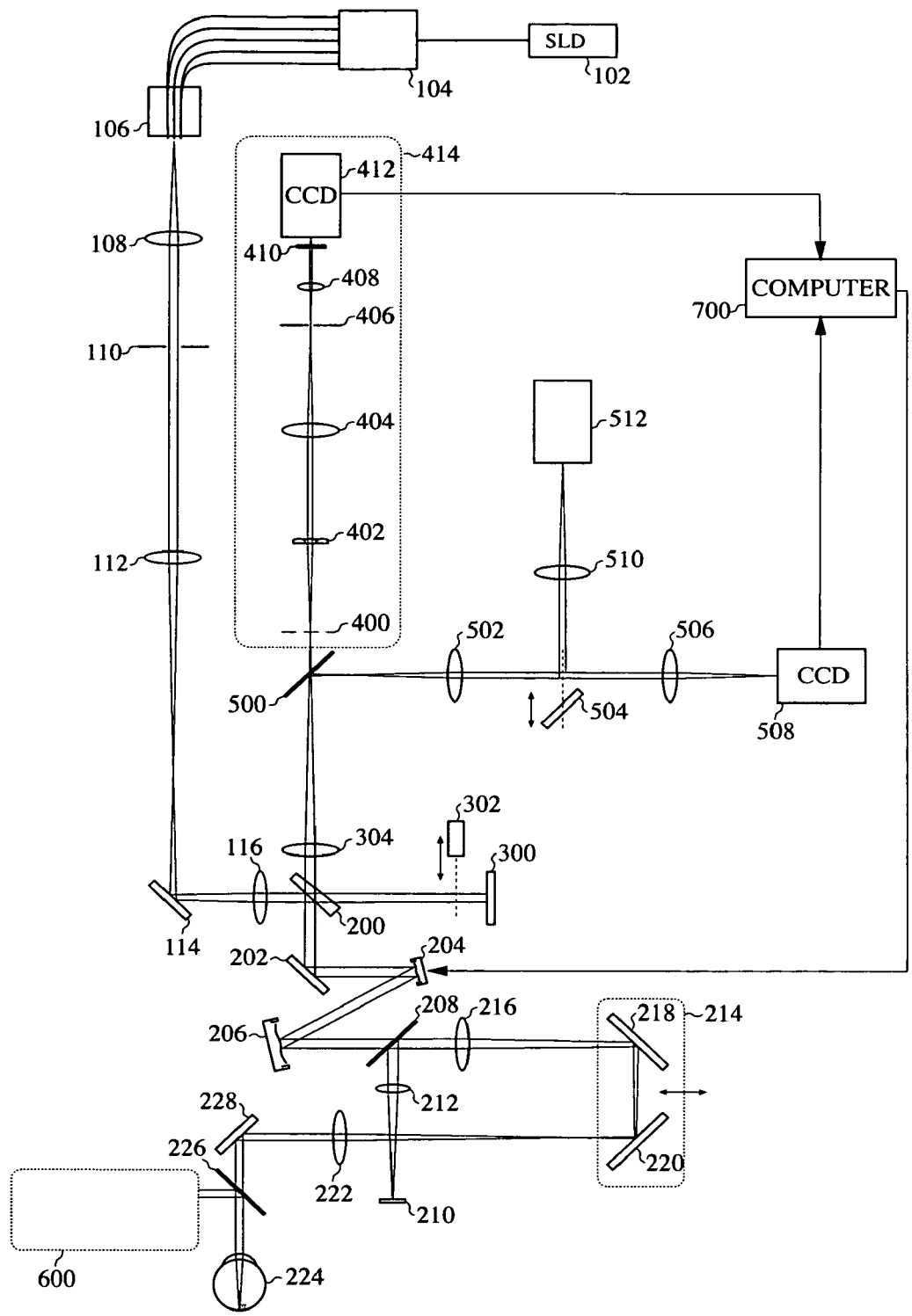

FIG. 2 shows the layout of the MCAO setup for retinal imaging and psychophysical testing. An explanation is given in Example 1.

Figure 3A:
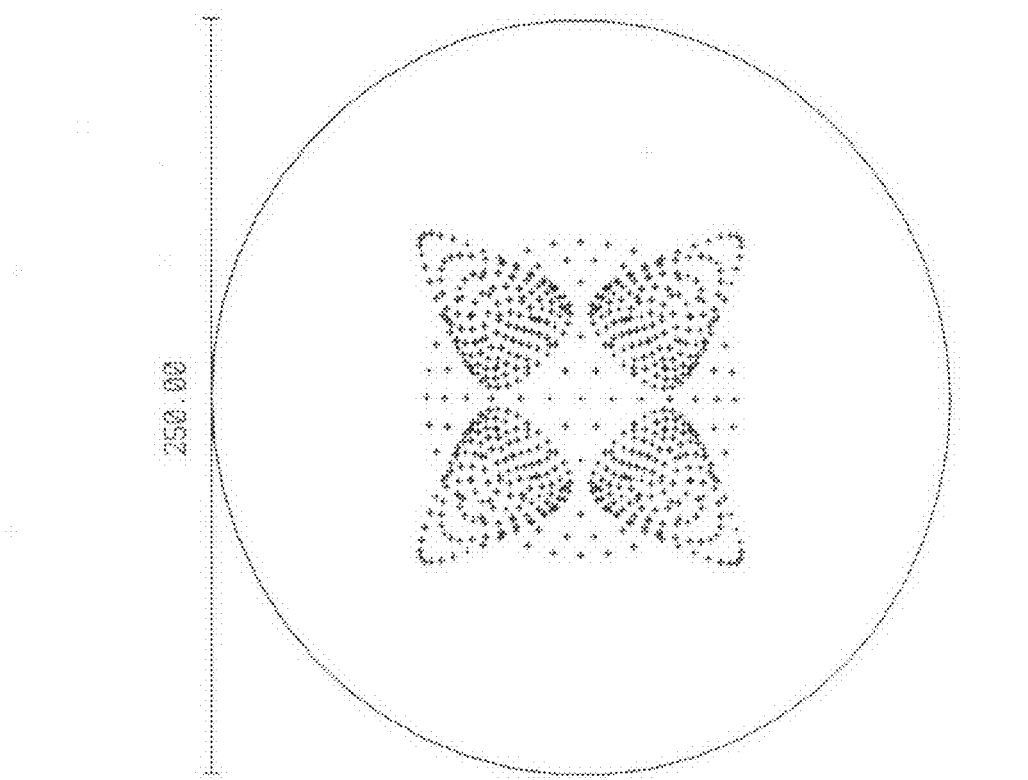

FIG. 3a shows a simulation using the optical software package ZEMAX (ZEMAX Development Corporation, Bellevue Wash., USA) of the layout of the multiple focused reference source images in the plane of the WFS pinhole 406. Scale bar is 250 microns.

Figure 3B:
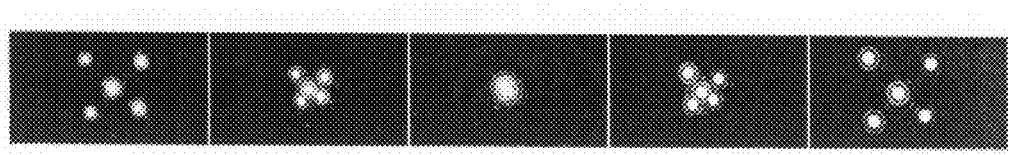

FIG. 3b shows actual images of the multiple focused reference source images, the two leftmost images just in front of the plane of the WFS pinhole 406, the middle image in the plane of the WFS pinhole 406, and the two rightmost images just after the plane of the WFS pinhole 406.

Figure 4A:
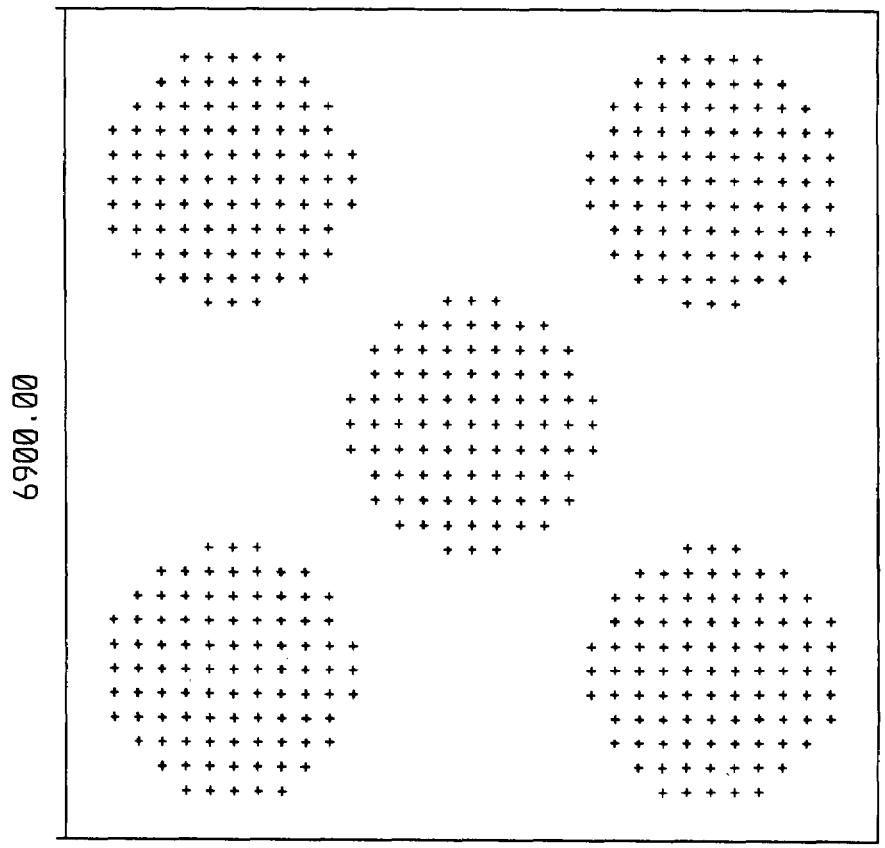

FIG. 4a shows a ZEMAX simulation of the layout of the multiple Hartmann images on the WFS camera 412. Scale bar is 6900 microns.

Figure 4B:
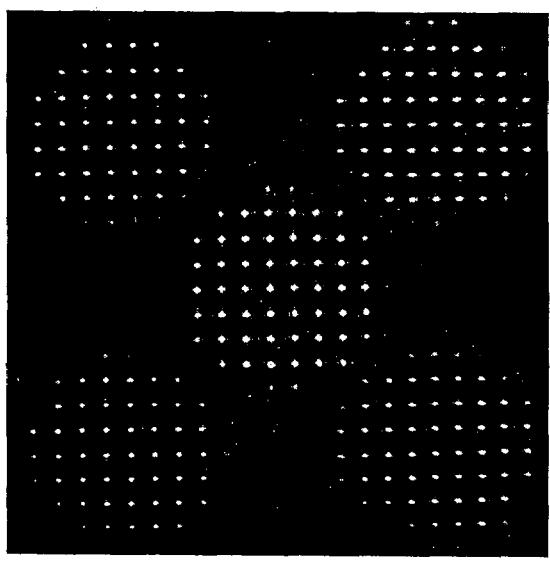

FIG. 4b shows the real multiple reference Hartmann images on the WFS camera 412.

Figure 4C:
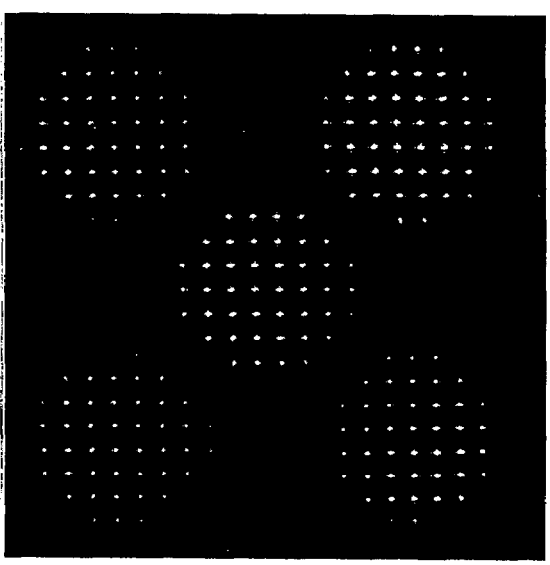

FIG. 4c shows the real multiple measurement Hartmann images on the WFS camera 412.

DETAILED DESCRIPTION OF THE INVENTION AND PREFERRED EMBODIMENTS THEREOF

The invention can be described as a multi-object Shack-Hartmann wavefront sensor with spatial filtering. Input to the sensor is a telecentric focal plane for the aberrated reference source images. Crucial sensor components are: (i) a collimator array in combination with a lens forming overlapping images of the reference sources; (ii) a simple adjustable spatial filter eliminating unwanted light contaminating the wavefront measurements for all sources; (iii) a lens providing simultaneous match to the camera target size of the reference wavefronts; (iv) a microlens array sampling the source wavefronts and providing multiple source images on a camera target; and (v) a camera, which is sufficiently fast and sensitive to catch the dynamical wavefront slopes.

Our invention, by firstly using an array of collimator lenses, makes it possible to simultaneously measure wavefront slopes of several reference sources on a single detector. The wavefront slopes can be processed to provide multiple wavefronts intended for aberration analysis. The wavefront slopes can also be processed to provide simultaneous inputs for several aberration-compensating devices such as deformable mirrors and reflecting or transmitting phase modulators. Used in close loop mode the rejection of spurious signals can be improved, and secondly this arrangement makes it possible to spatially filter the light from all reference sources using one focusing lens and one variable pinhole.

Specifically the invention herein is a wavefront sensor comprising means for detecting irradiance and determining wavefront for multiple sources in combination with means for rejection of spurious irradiance and means for analyzing output of said detecting means. Preferably the detection means comprises a single camera. The camera comprises e.g. a charge-coupled device (CCD) providing electrical output to analyzing means. The detection of multiple source irradiation is preferably obtained using a collimator array matched to said sources and a microlens array, and the rejection of spurious irradiance is obtained forming overlapping source images and passing said overlapping source images through a variable pinhole. The means for analyzing output of said detection means may comprise a personal computer.

Typical areas of application are wide field retinal imaging, psychophysical investigation of subjective image perception of humans, astronomical multi-reference wavefront sensing, communication systems, and image transfer.

The features of the present invention will be more clearly understood by reference to the following examples, which are not to be construed as limiting the invention.

EXAMPLE 1

In the following we describe, the use of the sensor in connection with retinal imaging (overview in FIG. 2).

Light Delivery

As shown in FIG. 2, continuous relatively broadband near-infrared light from a super-luminescent diode (SLD) 102 is fed through a pigtailed single mode fiber to a 1-to-5 single mode fiber splitter 104. The five single mode fibers are connected to an adjustable fiber holder 106 that feeds the light through five single mode fibers. The fiber ends, arranged in a cross with a center-to-center displacement of 3.5 mm, are positioned at the focal plane of a collimating lens 108, and light fed through the fiber ends forms five separate collimated ray-bundles after the collimating lens 108. The bundles pass a pupil 110 and are coupled into the main light path via lens 112, a mirror 114, and a lens 116.

Part of the light is diverted by a wedge beam splitter (WBS) 200 and a mirror 202 towards two deformable mirrors (DM) 204 and 206 (OKO Technologies, Delft, The Netherlands). DM 204 has a 15 mm mirror surface and 37 actuators, while DM 206 has a 40 mm mirror surface and 79 actuators. The light passes a pellicle beam splitter 208 (PBS), used to direct light from a fixation cross 210 via a lens 212 into the light path, and continues through lens 216 via a focus adjustment system (Badal system) 214 made up of mirrors 218 and 220, and through lens 222. The light finally enters the eye 224 via a mirror 228 and a second PBS 226. The Badal system 214 is used to correct for a subject's spherical refractive error, and passing the guide star light through the Badal system 214 ensures the delivery of well-focused spots on the retina. The five spots imaged on the retina are arranged in a cross with a center-to-center displacement of 600 μm (2.2 deg), each guide star with a full width at half maximum (FWHM) of approximately 30 μm.

The remainder of the of the guide star light passes through the WBS 200, reflects off mirror 300, and is again reflected by the WBS 200, but this time towards the wavefront sensor (WFS) 414. This light is used to form the Hartmann-Shack calibration. It passes through lens 304 and is focused through a cold mirror (CM) 500 to a telecentric WFS front focal plane 400. It is critical that both the calibration and wavefront sensing arms have a focus at this spot in order to ensure conformity. The light then passes a collimating lens array (CLA) 402 with five collimating lenses (FIG. 1b), and a focusing lens 404. Lens 404 focuses all source rays on top of each other on the optical axis in the plane of a variable pinhole 406 (see also FIG. 1a). This enables the elimination of unwanted light contaminating the wavefront measurements for all sources. The light is again collimated by lens 408 before being imaged by a microlens array (LA) 410 onto the WFS camera 412.

Wavefront Sensing

In the wavefront sensing arm, reflected light travels through the optical media of the eye 224 and emerges through the pupil as five aberrated wavefronts, one from each guide star. They pass through the Badal system 214, and are thus compensated for the subject's defocus. This is done in order to conserve DM corrective power. The stroke of a DM, which determines its corrective power, is limited and the corrected amount of defocus can always be added computationally at a later time. The wavefronts first reflect off DM 206, conjugated to a plane inside the eye close to the retina, before reflecting off DM 204, conjugated to the pupil of the eye. The light then passes through the WBS 200, a relay lens 304, and the CM 500, before passing through the CLA 402: This arrangement makes it possible to spatially filter the light from all five guide stars using one focusing lens 404 and one variable pinhole 406. The light is finally collimated by a lens 408 and imaged by the LA 410 onto the WFS camera 412. The Hartmann pattern images formed on the camera are continuously analyzed by a computer 700 in order to calculate the corrections that are to be applied to the two DMs 204 and 206.

Imaging and Psychophysics

In the arm used for imaging and/or psychophysics light can travel in two directions. When the instrument is to be used in imaging mode, light from a flash delivery system 600 will illuminate the retina via a PBS 226 located just in front of the eye. Light returning through the system will be diverted by the CM 500 and relayed through lenses 502 and 506 to an imaging camera 508. When the system is to be used in psychophysical mode a flip mirror 504 will be raised between lenses 502 and 506, relaying a psychophysical test image 512 through lens 502 and the CM 500 towards the eye 224. In passing the two DMs 204 and 206 and the Badal system 214, it will be compensated with respect to the eye's aberrations and thus form an unaberrated image on the retina.

EXAMPLE 2

A simulation was made (see FIG. 3a) using the optical software package ZEMAX (ZEMAX Development Corporation, Bellevue Wash., USA) of the layout of the multiple focused source images in the plane of the WFS pinhole 406. The scale bar is 250 microns.

FIG. 3b shows actual images of the multiple focused source images, the two leftmost images just in front of the plane of the WFS pinhole 406, the middle image in the plane of the WFS pinhole 406, and the two rightmost images just after the plane of the WFS pinhole 406. FIG. 4a shows a ZEMAX simulation of the layout of the multiple Hartmann images on the WFS camera 412. Scale bar is 6900 microns. FIG. 4b shows the real multiple reference Hartmann images on the WFS camera 412 and FIG. 4c shows the real multiple measurement Hartmann images on the WFS camera 412.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A wavefront sensor comprising:
    a) means for detecting irradiance and determining wavefronts for multiple sources;
    b) means for rejection of spurious irradiance from the multiple sources; and
    c) means for analyzing output of said detecting means.

2. The wavefront sensor of claim 1, wherein the means for detecting irradiance comprises a single camera.

3. The wavefront sensor of claim 2, wherein the camera provides electrical output to the analyzing means.

4. The wavefront sensor of claim 1, wherein detection of multiple source irradiation is obtained using a collimator array matched to said sources and a lenslet array.

5. The wavefront sensor of claim 1, wherein said the means for rejection of spurious irradiance is obtained by forming overlapping source images and passing said overlapping source images through a fixed or variable pinhole.

6. The wavefront sensor of claim 1, wherein the means for analyzing output of said detecting means comprises computer software for analysis and hardware.

7. A method of measuring high-order aberrations in living human eyes, comprising providing a wavefront sensor according to claim 1 with spatial filtering in an adaptive optics system.

8. A wavefront sensor comprising:
(a) a collimator array in combination with a lens forming overlapping images of multiple reference sources;
(b) a simple adjustable spatial filter eliminating unwanted light contaminating wavefront measurements for all sources;
(c) a lens providing simultaneous match to a camera target size of reference wavefronts;
(d) a microlens array sampling source wavefronts and providing multiple source images on a camera target; and
(e) a camera, which is sufficiently fast and sensitive to catch dynamical wavefront slopes.

\* \* \* \* \*